United States Patent
Grimm et al.

(10) Patent No.: US 6,855,816 B1
(45) Date of Patent: Feb. 15, 2005

(54) METHOD FOR PRODUCING ENDOTOXIN-FREE NUCLEIC ACIDS AND THE USE THEREOF

(75) Inventors: Stefan Grimm, München (DE); Frank Neudecker, München (DE)

(73) Assignee: Xantos Biomedicine AG, Munich (DE)

( * ) Notice: Subject to any disclaimer, the term of this patent is extended or adjusted under 35 U.S.C. 154(b) by 0 days.

(21) Appl. No.: 09/890,202

(22) PCT Filed: Jan. 26, 2000

(86) PCT No.: PCT/EP00/00564

§ 371 (c)(1),
(2), (4) Date: Nov. 5, 2001

(87) PCT Pub. No.: WO00/44759

PCT Pub. Date: Aug. 3, 2000

(30) Foreign Application Priority Data

Jan. 29, 1999 (DE) .......................................... 199 03 507

(51) Int. Cl.[7] ........................ C07H 21/00; C07H 21/02; C07H 21/04; C12N 15/63
(52) U.S. Cl. .................... 536/25.4; 435/320.1; 435/455
(58) Field of Search ............................ 536/25.4, 25.41, 536/23.1; 435/320.1, 455; 514/44

(56) References Cited

U.S. PATENT DOCUMENTS

| | | | |
|---|---|---|---|
| 4,997,932 A | | 3/1991 | Reardon et al. |
| 5,693,785 A | * | 12/1997 | Woodard et al. ............ 536/25.4 |
| 5,747,663 A | | 5/1998 | Colpan et al. |
| 5,792,651 A | | 8/1998 | Colpan et al. |
| 6,110,363 A | * | 8/2000 | Hillebrand et al. ...... 210/198.2 |
| 6,194,562 B1 | * | 2/2001 | Smith et al. ................ 536/24.5 |
| 6,277,648 B1 | | 8/2001 | Colpan et al. |
| 6,297,371 B1 | * | 10/2001 | Colpan et al. ............. 536/25.3 |
| 2001/0041332 A1 | | 11/2001 | Hillebrand et al. |

FOREIGN PATENT DOCUMENTS

| | | |
|---|---|---|
| AU | 199862084 B2 | 8/1998 |
| WO | WO 95/21178 A1 | 8/1995 |
| WO | WO 97/29113 A2 | 8/1997 |

OTHER PUBLICATIONS

Grimm et al. High–purity plasmid isolation using silica oxide. Method Mol. Biol. 235:83–87, 2003.*
Horn et al. Cancer gene therapy using plasmid DNA: Purification of DNA for human clinical trials. Human gene therapy 6:565–573, 1995.*
Wang, Lu, et al., "Purification of genomic DNA from human whole blood by isopropanol–fractionation with concentrated NaI and SDS," *Nucleic Acids Research* 22(9):1774–1775, 1994.

* cited by examiner

*Primary Examiner*—David Guzo
*Assistant Examiner*—Quang Nguyen
(74) *Attorney, Agent, or Firm*—Rothwell, Figg, Ernst & Manbeck p.c.

(57) ABSTRACT

Method for isolating and purifying nucleic acids and/or oligonucleotides from a biological sample, the use of the isolated or purified nucleic acid and/or oligonucleotide for transfecting cells and also for the production of an agent for the treatment of genetic disorders, a composition suitable for the isolation or purification method and also the use of potassium acetate and a silica gel-like support material for isolating endotoxin-free nucleic acids and/or oligonucleotides or nucleic acids and/or oligonucleotides with reduced endotoxin content.

13 Claims, 1 Drawing Sheet

METHOD FOR PRODUCING ENDOTOXIN-FREE NUCLEIC ACIDS AND THE USE THEREOF

This application is a 371 of International Application No. PCT/EP00/00564, filed Jan. 26, 2000, which claims priority from German Application No. DE 199 03 507.5, filed Jan. 29, 1999.

BACKGROUND OF THE INVENTION

1. Technical Field

The invention relates to a method for isolating and purifying nucleic acids and/or oligonucleotides from a biological sample, to the use of the isolated or purified nucleic acid and/or oligonucleotide for transfecting cells and also for the production of an agent for the treatment of genetic disorders, to a composition suitable for the isolation or purification method and also to the use of potassium acetate and a silica gel-like support material for isolating endotoxin-free nucleic acids and/or oligonucleotides or nucleic acids and/or oligonucleotides with reduced endotoxin content.

2. Description of the Background Art

The quality of isolated nucleic acids is becoming increasingly important. Highly pure nucleic acid fractions, i.e. fractions from which, if possible, all other cell components such as, for example, endotoxins, have been removed, play a central part in gene therapy or in transfecting cells of eukaryotic or also prokaryotic origin. Consequently, in the past few years methods or measures which allow the isolation of nucleic acids from biological sample material with high purity have increasingly been published. The established methods essentially make use of the use of affinity and/or anile exchange chromatography materials and also of ionic detergents or also diluted solutions of higher alcohols. For example, according to WO95/21177 the fractions of interest are subjected to an affinity chromatography or a chromatography on an inorganic solid phase, the latter preferably in the presence of a non-ionic detergent, in order to remove endotoxins and are then further purified by means of anion exchange chromatography. A two-stage chromatography method of this kind, however, is time- and material-consuming and therefore is more academically valuable. According to another method (WO95/21178) a complicated anion exchange chromatography is likewise absolutely necessary in order to remove residues of a complex salt solution added beforehand.

Furthermore, it has been known for some time that DNA plasmids from complex biological samples of eukaryotic or prokaryotic origin can be isolated by binding to silica gel in the presence of chaotropic salts such as, for example, guanidine hydrochloride (M. A. Marko et al., *Analyt. Biochem.* 121, (1982) 382–287; EP 0 389 063). However, these methods are not suitable for obtaining low-endotoxin or endotoxin-free nucleic acid fractions. Thus it has been possible to show, for example, that the measures according to Marko et al. (1982) lead to an endotoxin content of more than 10,000 Upper mg of DNA. Such an endotoxin-rich DNA fraction is unsuitable for transfecting cells in applications of gene therapy.

SUMMARY OF THE INVENTION

It was therefore the object of the invention to provide a method for preparing endotoxin-free nucleic acids or nucleic acids with reduced endotoxin content, as a result of which the disadvantages of established methods, such as in particular complicated column materials, are avoided.

DETAILED DESCRIPTION OF THE PREFERRED EMBODIMENTS

Figure 1:
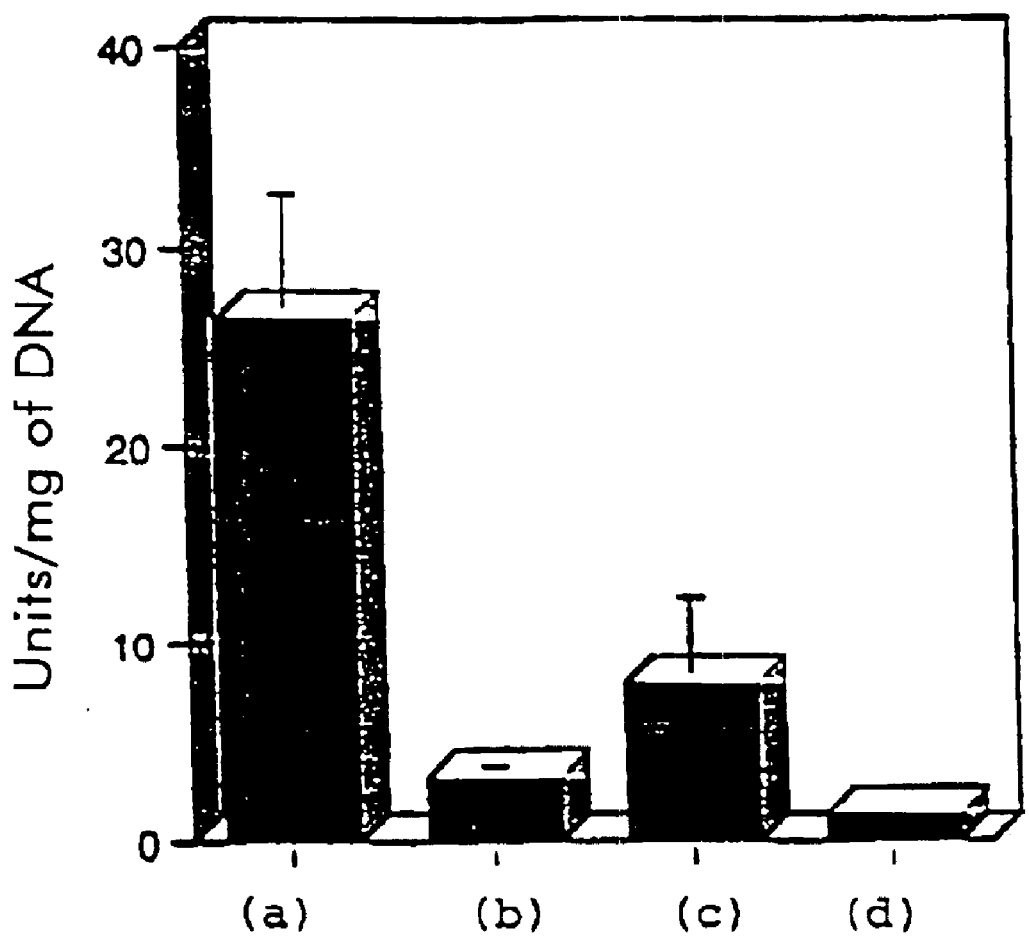
FIG. 1 provides endotoxin (lipopolysaccharidej LPS) content in various DNA plasmid fractions after acetone washing ((c), (d)) and SDS precipitation ((b), (d)) with washing using isopropanol ((a), (b)) or acetone ((c), (d)), with or without LPS precipitation in the presence of SDS (2.5% in isopropanol).

The object is achieved by a method for isolating and purifying nucleic acids and/or oligonucleotides from biological samples, in which the particular biological sample is disrupted, undissolved cell components are resuspended in an aqueous potassium acetate solution, optionally present insoluble components are removed, for example by centrifugation, and the aqueous phase is mixed and incubated with an alcoholic solution containing a detergent. The solution is then contacted with a silica gel-like support material, the aqueous phase is, if possible, quantitatively removed from the support material binding the nucleic acids or oligonucleotides, for example by suction or centrifugation, and the support material with the DNA is then washed adequately. The washing solution used may be an alcoholic solution or acetone which has proved particularly advantageous. Depending on the volume of the starting sample, an incubation time for contacting the support material of from to not more than 40 minutes at room temperature is sufficient; according to the invention, approx. 20 minutes are normally sufficient.

The skilled worker in principle knows silica gel-like support materials. According to the invention, a suspension of silicon dioxide has proved particularly suitable. A silicon oxide suspension which was prepared by adding acid (e.g. hydrochloric acid) to an aqueous suspension of silicon dioxide and was then autoclaved is particularly suitable for the method of the invention.

The aqueous potassium acetate solution contains potassium acetate preferably in a concentration range from approx. 1 to 6 mol/l, and a range from 2 to 4 mol/l and a weakly acidic pH (approx. pH 4.5–6.8) have resulted, according to the invention, in a particularly high quality of the nucleic acids.

Another advantageous embodiment of the method of the invention is to add to the sample, after addition of the potassium acetate solution, additionally one or more RNA-digesting enzymes such as, for example, RNAse A and/or RNAse T1. In particular for relatively large preparations it has proved advantageous to add the RNA-digesting enzyme(s) in the same medium/buffer in which the potassium acetate salt had been added before. Alternatively, and this is particularly true for relatively small mixtures, the RNA-digesting enzymes can also be added even during disruption of the biological sample, i.e. together with the lysis buffer (e.g. together with buffer (1 in example 1.2). If a plurality of RNA-digesting enzymes is added, said enzymes may be present in any ratios or else in equal parts. The final concentration of RNA-digesting enzymes in said solution is normally up to or at approx. 150 mg/ml; but even higher enzyme concentrations have not had an adverse effect on the method of the invention.

Normally, according to the invention, an incubation with the potassium acetate solution of from 5 to 10 minutes at 4° C., where appropriate initially at room temperature, is already sufficient for the enzymatic digestion; depending on the amount of sample material used, however, the incubation may be extended accordingly.

Suitable alcoholic solutions according to the invention are in particular high percentage solutions of higher alcohols such as isopropanol. According to the invention, it has proved particularly advantageous if the alcoholic solution is not diluted with water, that is to say virtually 100% of it consists of the particular alcohol, and it additionally contains one or more ionic detergents, at a concentration of 0.5 to 10% (w/v). A 100% isopropanol solution containing approx. 1 to 4% (w/v) SDS has proved particularly suitable according to the invention.

The biological sample can in principle be disrupted or pre-purified according to methods known to the skilled worker. According to the invention, preference is given to alkaline lysis measures, in particular in the case of bacterial host cells. In this way it is possible to remove protein components and other soluble components before contacting the residue which essentially contains nucleic acid components and other non-soluble cell components with the potassium acetate solution or the alcohol/detergent solution.

Using the method of the invention it is possible to obtain nucleic acids such as, for example, plasmid DNA in high quality, i.e. in particular with an endotoxin content of less than 100 U/mg of DNA, normally of not more than 10 U/mg of DNA.

In particular it must be regarded as surprising that the DNA can be bound with high efficiency to the adsorption matrix after alkaline lysis without the need for the addition of chaotropic substances as described in the prior art. The absence of added chaotropic substances leads to substantial improvements and purifications in the subsequent DNA purification procedure and/or in the corresponding transfection of target cells, that is for cells of both eukaryotic and prokaryotic origin.

Moreover, the endotoxin-free nucleic acids and/or oligonucleotides or the nucleic acids and/or oligonucleotides with reduced endotoxin content, which are obtainable according to the method of the invention, are suitable for producing agents for the treatment of genetic diseases.

The invention further relates to means or compositions for obtaining plasmid DNA from appropriate host cells, which can be, for example, microtiter plates or blocks which may, where appropriate, contain mini columns for purifying plasmid DNA.

The compositions of the invention essentially contain an aqueous potassium acetate solution and also a detergent-containing alcoholic solution and a silica gel-like support material. Moreover, it is advantageous if a solution suitable for disrupting a biological sample, in particular for alkaline lysis, is present. In particular embodiments of the composition the salt concentration in the potassium acetate solution is in a range from approx. 1 to 6 M, particularly preferably from approx. 2 to 4 M in a weakly acidic medium (pH approx. 4.5–6.8), the alcoholic solution contains isopropanol with approx. 0.5 to 10% (w/v) of an ionic detergent such as, for example, SDS and/or the support material is an aqueous suspension of silicon dioxide.

FIG. 1

Endotoxin (lipopolysaccharide, LPS) content in various DNA plasmid fractions after acetone washing ((c), (d)) and SDS precipitation ((b), (d)). The plasmid DNA was isolated by binding to silicon oxide and subsequently washed with isopropanol ((a), (b)) or acetone ((c), (d)), with or without LPS precipitation in the presence of SDS (2.5% in isopropanol). The LPS content was determined calorimetrically, according to the manufacturer's instructions (Boehringer Ingelheim, Germany).

(a) isopropanol/without SDS,
(b) isopropanol/with SDS,
(c) acetone/without SDS,
(d) acetone/with SDS The following examples further illustrate the invention:

EXAMPLES

Example 1.1 Cell Culture and Transfection.

Baby hamster kidney (BHK) cells were cultured in DMEM (Dulbecco's Modified Eagle's Medium) supplemented with 5% fetal calf serum (Sigma, Deisenhofen, Germany) in a humidified 5% $CO_2$ atmosphere. For transfections, the cells were applied to 24-well plates and transfected with 2 mg of plasmid DNA according to the calcium phosphate coprecipitation method as described by Roussel et al. (Mol. Cell. Biol. 4 (1984), 1999–2009). For this purpose, 25 ml of DNA solution were mixed with 25 ml 2×HBS: 274 mM NaCl, 10 mM KCl, 40 mM HEPES, 1.4 mM $Na_2PO_4$, pH 6.9 at 4° C. in a 96-well plate using a 12-channel pipette (Eppendorf, Hamburg, Germany). After adding 20 ml of a 0.25 M $CaCl_2$ solution (4° C.) and mixing, 38 ml were added to the cells after incubation at room temperature for 25 min.

Appropriate aliquots were inoculated in 900 ml of TB medium in wells of 96-well blocks (Qiagen, Hilden, Germany) and cultured with shaking at 300 rpm for approx. 30 hours (37° C.). After identification of a positive pool, the DNA was again transfected to confirm the result. The remaining DNA was used to transform bacteria for large-scale plasmid isolation.

Example 1.2 Plasmid isolation with Columns.

96-well blocks (Qiagen, Hilden, Germany) with bacteria were centrifuged at 3000 g (Sigma centrifuges, Osterode am Harz, Germany) for 5 min. The supernatant was decanted and the blocks were inverted and put on absorbent paper towel for 2 to 3 min. Then 170 ml of buffer P1 (50 mM Tris-HCl/10 mM EDTA pH 8.0, 4° C.) were added and the bacteria pellets were resuspended by complete vortex treatment for 10 to 20 min. After addition of 170 ml of buffer P2 (200 mM NaOH, 1% SDS), the block was sealed with foil, inverted and incubated at room temperature for 5 min. The lysis was stopped by adding 170 ml of 4° C. cold buffer P3 (3 M potassium acetate pH 5.5, 4° C.). Then 10 ml of RnaseA solution (1.7 mg/ml) were added, followed by incubation at room temperature and then at −20° C. for 5 min and another centrifugation at 6000 rpm for 10 min. The supernatant was decanted into new blocks and 100 ml of buffer P4 (2.5% (w/v) SDS in isopropanol) were added. The block was subjected to vortexing for 5 min and incubated initially at 4° C. for 15 min and then at 20° C. for 15 min. The blocks were centrifuged at 6000 rpm for 10 min and the supernatant was transferred into an array of 96 columns (Qiagen) in appropriately cut 96-well plates. These plates were placed in vacuum chambers (Qiagen). Then 150 ml of silicon oxide suspension were added followed by incubation at room temperature for 20 min (the silicon oxide suspension was prepared by adding 150 ml of HCl (37%) to 250 ml of a suspension of 50 mg/ml $SiO_2$ (Sigma) and subsequent autoclaving).

After applying reduced pressure, the columns were washed twice with 600 ml of acetone (−20° C.). The 96-well column plate was put on a 96-well microtiter plate and centrifuged at 6000 rpm for 4 min. The column plate was dried initially at 37° C. for 5 min and then in a vacuum chamber for 5 min and then put on another microtiter plate. 70 ml of double-distilled H₂O (60° C.) were added followed by centrifugation at 6000 rpm for 3 min. The microtiter plate was stored at −20° C.

Example 1.3 Plasmid Isolation Without Columns.

Up to the addition of buffer P4, the method was carried out as described under point 1.2. After centrifugation at 6000 rpm for 10 min, the supernatant was then provided to 96-well POM-microtiter blocks (POM=polyoxymethylene) and 150 ml of silicon oxide suspension were added followed by incubation at room temperature for 20 min. The plates were centrifuged at 6000 rpm for 5 min. The supernatant was carefully decanted and 400 ml of acetone (−20° C.) were added. The plates were again vortexed (30 sec) and centrifuged at 6000 rpm for 3 min. This acetone washing was repeated once. The plates were dried initially at room temperature for 5 min and then in a vacuum chamber for 5 min. The pellets were resuspended in 75 ml of water (60° C.) and centrifuged at 6000 rpm and 4° C. for 10 min. The supernatant was stored in a 96-well microtiter plate at −20° C.

Example 2

Results

Plasmid DNA was isolated from the bacteria cultures using mini columns (see point 1.2). A corresponding protocol without columns is described under point 1.3.

It is important for the transfection step to obtain plasmid DNA of very high purity. For this purpose, silicon dioxide was used as binding matrix for plasmid DNA. Binding; of DNA and silicon dioxide in the presence of chaotropic substances is well known (Vogelstein and Gillespie, *Proc. Natl. Acad. Sci. USA* 76 (1979), 615–619). Surprisingly, however, it was found that even in the absence of an added chaotropic substance such as, for example, guanidine hydrochloride, the plasmid DNA binds to silicon dioxide with sufficient capacity. After subsequent washing in acetone, where appropriate with the addition of SDS, plasmid DNA in excellent quality, corresponding to a purification via a cesium chloride gradient, could be obtained. Commonly, about 10 mg of plasmid DNA with an OD260/280 of greater than 1.8 were obtained from 900 ml of LB medium, 90% of which were present in supercoiled form.

Example 3

Comparison with Prior Art

Experiment A: Bacteria culture: *E. coli* HB101 pCMVbetaSportGAL, $OD_{680}$/ml approx. 3.3

In duplicate mixtures, 1.8 ml each of bacteria culture were worked up using the High Pure plasmid isolation kit (Boehringer Mannheim, Cat. No. 1 754 777), which contains a glass-like support material and a strongly chaotropic salt and 1.8-ml each of bacteria culture were processed according to the method of the invention.
The result is as follows:

| Yield $OD_{260}$ nm: | Endotoxin content (LAL assay) |
|---|---|
| High Pure 1: 9.0 mg/100 ml of endotoxin-free water | 214 EU/mg of plasmid |

-continued

| Yield $OD_{260}$ nm: | Endotoxin content (LAL assay) |
|---|---|
| High Pure 2: 8.6 mg/100 ml of endotoxin-free water | 240 EU/mg of plasmid |
| Invention 1: 11.00 mg/100 ml of endotoxin-free water | 1.41 EU/mg of plasmid |
| Invention 2: 10.35 mg/100 ml of endotoxin-free water | 4.65 EU/mg of plasmid |

Procedure according to the method of the invention using a High Pure filter tube:
The bacteria culture was centrifuged at 13,000 rpm for 30 sec and the supernatant was removed.
The cell pellet of 1.8 ml of bacteria culture was further treated as follows:
1. Resuspending in 250 ml of 50 mM Tris-HCl/10 mM EDTA, 100 mg of RNase (DNase-free), pH 8.0, 4° C.
2. Adding 250 ml of 0.2 M NaOH, 1% SDS and 5–10× inverting the vessel, 5 min at room temperature.
3. Adding 250 ml of 3 M K acetate (4° C.) and 5–10× inverting the vessel, incubating on ice for 5 min.
4. Centrifuging in a bench-top centrifuge at maximum speed for 10 min (14,000 rpm), removing the supernatant and adding 0.2 vol. (approx. 150 ml) of 2.5% SDS in isopropanol (e.g. 7 ml of isopropanol and 1 ml of 20% SDS) and vortexing briefly, incubating at 4° C. for 15 min and then incubating at −20° C. for 15 min.
5. Centrifuging in a bench-top centrifuge at maximum speed for 10 min (14,000 rpm), removing supernatant.
6. Pipetting supernatant into High Pure filter tube and incubating at room temperature for 20 min.
7. Centrifuging in a bench-top centrifuge at maximum speed for 30 sec (14,000 rpm), discarding the flow-through and washing the filter tube 2× with 700 ml of ice-cold acetone (centrifuging between the washing steps at 14,000 rpm for 30 sec).
8. After the last washing step, centrifuging again at 14,000 rpm for 30 sec in order to dry the fleece.
9. Eluting DNA by adding 100 ml of endotoxin-free water and incubating at room temperature for 10 min. The DNA is obtained by centrifuging at maximum centrifugation speed for 30–60 sec.

Experiment B: Bacteria culture: *E. coli* JM109 pCMVbetaSportGal $OD_{580}$/ml 2.37

| Sample | Method | Modification | Yield [mg/100 mg] | Endotoxin [EU/mg] |
|---|---|---|---|---|
| 1 and 2 | High Pure | | 9.3/9.3 | 371.7 |
| 3 and 4 | High Pure | Incubated on fleece for 20 min; incubated before elution for 10 min | 12.8/12.2 | 2.18 |
| 5 and 6 | Invention | Without incubations | 12.2/12.6 | 0.63 |

Result:
The method of the invention shows approx. 100 fold reduction in endotoxin.
Furthermore, the inventive method with rapid passing through by centrifugation gives the same yield as using incubation on fleece, and therefore the purification time can not be stated as approx. 70 min. In addition, the inventive method with rapid passing through by centrifugation shows a lower endotoxin value than after incubation on fleece.

We claim:

1. A method for isolating and purifying nucleic acids and/or oligonucleotides from a biological sample, said method comprising:
   (a) disrupting the biological sample;
   (b) optionally removing protein and insoluble components from said disrupted sample;
   (c) adding an aqueous solution of potassium acetate to said disrupted sample and subsequently separating non-soluble components from the aqueous solution;
   (d) mixing said aqueous solution of potassium acetate containing said disrupted sample with an alcoholic solution containing SDS;
   (e) incubating said mixed solution;
   (f) obtaining the supernatant of said mixed solution;
   (g) contacting and incubating said supernatant with a suspension of silicon dioxide or silica gel to produce a bound fraction and a soluble fraction; and
   (h) isolating purified nucleic acids and/or oligonucleotides from said bound fraction.

2. The method as claimed in claim 1, wherein said alcoholic solution comprises SDS at a concentration of 0.5% to 10% (w/v) in 100% strength alcohol.

3. The method as claimed in claim 1, wherein said aqueous solution of potassium acetate of step (c) comprises 1 M to 6 M potassium acetate.

4. The method as claimed in claim 3, wherein said aqueous solution of potassium acetate of step (c) comprises 2 M to 4 M potassium acetate.

5. The method as claimed in claim 1, wherein said bound fraction is washed at least once with acetone after step (g) and prior to step (h).

6. The method as claimed in claim 1, wherein said purified nucleic acids and/or oligonucleotides of step (h) contain less than 100 U/$\mu$g endotoxin.

7. The method as claimed in claim 6, wherein said purified nucleic acids and/or oligonucleotides of step (h) contain less than 10 U/$\mu$g plasmid DNA endotoxin.

8. A method of transfecting eukaryotic or prokaryotic cells with nucleic acids or oligonucleotides, said method comprising:
   (a) isolating and purifying nucleic acids and/or oligonucleotides from a biological sample by the steps of:
      (1) disrupting the biological sample;
      (2) optionally removing protein and insoluble components from said disrupted sample;
      (3) adding an aqueous solution of potassium acetate to said disrupted sample and subsequently separating non-soluble components from the aqueous solution;
      (4) mixing said aqueous solution of potassium acetate containing said disrupted sample with an alcoholic solution containing SDS;
      (5) incubating said mixed solution;
      (6) obtaining the supernatant of said mixed solution;
      (7) contacting and incubating said supernatant with a silicon dioxide support material to produce a silicon dioxide bound fraction and a soluble fraction; and
      (8) isolating purified nucleic acids and/or oligonucleotides from said silicon dioxide bound fraction, and
   (b) transfecting said cells with said purified nucleic acids and/or oligonucleotides.

9. A method of producing a purified nucleic acid and/or oligonucleotide composition suitable for use in the treatment of genetic disorders, said method comprising isolating and purifying nucleic acids and/or oligonucleotides from a biological sample by the steps of:
   (a) disrupting the biological sample;
   (b) optionally removing protein and insoluble components from said disrupted sample;
   (c) adding an aqueous solution of potassium acetate to said disrupted sample and subsequently separating non-soluble components from the aqueous solution;
   (d) mixing said aqueous solution of potassium acetate containing said disrupted sample with an alcoholic solution containing SDS;
   (e) incubating said mixed solution;
   (f) obtaining the supernatant of said mixed solution;
   (g) contacting and incubating said supernatant with a silicon dioxide support material to produce a silicon dioxide bound fraction and a soluble fraction; and
   (h) isolating purified nucleic acids and/or oligonucleotides from said silicon dioxide bound fraction.

10. A kit comprising:
    (a) at least one solution suitable for the disruption of a biological sample;
    (b) an aqueous potassium acetate solution;
    (c) an alcohol solution containing 0.5% to 10% (w/v) SDS in 100% strength isopropanol; and
    (d) a silicon dioxide support material.

11. A kit comprising:
    (a) a solution suitable for alkaline lysis and disruption of biological sample material;
    (b) an aqueous salt solution containing 1 M to 6 M potassium acetate;
    (c) an alcohol solution containing 0.5% to 10% (w/v) SDS in 100% strength isopropanol; and
    (d) a silicon dioxide support material.

12. A kit comprising:
    (a) at least one solution suitable for the disruption of a biological sample;
    (b) an aqueous potassium acetate solution;
    (c) an alcohol solution containing 0.5% to 10% (w/v) SDS in 100% strength isopropanol; and
    (d) a suspension of silicon dioxide or silica gel.

13. A kit comprising:
    (a) a solution suitable for alkaline lysis and disruption of biological sample material;
    (b) an aqueous salt solution containing 1 M to 6 M potassium acetate;
    (c) an alcohol solution containing 0.5% to 10% (w/v) SDS in 100% strength isopropanol; and
    (d) a suspension of silicon dioxide or silica gel.

* * * * *